(12) United States Patent
Su et al.

(10) Patent No.: US 8,375,804 B2
(45) Date of Patent: Feb. 19, 2013

(54) APPARATUS FOR TESTING BONDING STRENGTH OF ELECTRICAL CONNECTIONS AND FRICTIONLESS CALIBRATION DEVICE FOR THE SAME

(75) Inventors: Chia Ho Su, Kaohsiung (TW); Wen Sheng Lin, Hsinchu County (TW); Cheng Chieh Chen, Tainan County (TW)

(73) Assignee: Viswell Technology Co., Ltd., Hsinchu County (TW)

( * ) Notice: Subject to any disclaimer, the term of this patent is extended or adjusted under 35 U.S.C. 154(b) by 727 days.

(21) Appl. No.: 12/466,985

(22) Filed: May 15, 2009

(65) Prior Publication Data

US 2010/0288012 A1 Nov. 18, 2010

(51) Int. Cl.
*G01N 3/24* (2006.01)
*G01N 19/04* (2006.01)

(52) U.S. Cl. .......................... 73/842; 73/150 A; 73/843

(58) Field of Classification Search ............ 73/827–831, 73/841, 842, 760, 150 A
See application file for complete search history.

(56) References Cited

U.S. PATENT DOCUMENTS

| | | | | |
|---|---|---|---|---|
| 3,839,905 A * | 10/1974 | McCallen | ....................... | 73/848 |
| 5,767,414 A * | 6/1998 | Andrews et al. | ................ | 73/842 |
| 6,341,530 B1 * | 1/2002 | Sykes | ............................. | 73/842 |
| 6,564,115 B1 * | 5/2003 | Kinnaird | ....................... | 700/121 |
| 6,564,648 B2 * | 5/2003 | Lee et al. | ........................ | 73/842 |
| 7,597,006 B2 * | 10/2009 | Aiba | ............................... | 73/827 |
| 7,810,374 B2 * | 10/2010 | Zhang et al. | ................... | 73/841 |
| 2004/0103726 A1 * | 6/2004 | Cox | ................................ | 73/842 |
| 2009/0139303 A1 * | 6/2009 | Zhang et al. | ................ | 73/12.09 |
| 2010/0077867 A1 * | 4/2010 | Ihrke et al. | .............. | 73/862.041 |

* cited by examiner

*Primary Examiner* — Lisa Caputo
*Assistant Examiner* — Jonathan Dunlap
(74) *Attorney, Agent, or Firm* — WPAT, P.C.; Anthony King (57) ABSTRACT

An apparatus for testing bonding strength of electrical connection comprises a platform including a two-axis drive, a device holder positioned on the two-axis drive and configured to receive an electronic device, a vertical drive positioned on the platform, a cantilever positioned on the vertical drive, and a test head connected in a rotational manner with the cantilever. A frictionless calibration device for shear force testing comprises a base, two supporters positioned on the base, a shaft having two tapering ends positioned between the two supporters, and a calibration member fixed on the shaft, wherein the shaft and the calibration member contact the supporters in a rotational manner.

15 Claims, 8 Drawing Sheets

APPARATUS FOR TESTING BONDING STRENGTH OF ELECTRICAL CONNECTIONS AND FRICTIONLESS CALIBRATION DEVICE FOR THE SAME

BACKGROUND OF THE INVENTION (A) Field of the Invention

The present invention relates to an apparatus for testing bonding strength of electrical connections and a calibration device for the same, and more particularly, to an apparatus equipped with a rotational test head having at least two probes for testing the bonding strength of the electrical connection and a frictionless calibration device for the same.

(B) Description of the Related Art

Semiconductor devices have sites for the bonding of electrical conductors thereto; such sites typically comprise partly spherical deposits of gold or solder, collectively known as balls. It is necessary to test the mechanical strength of the bonding between the gold or solder balls and the substrate in order to give confidence that the bonding method is adequate, and that the bonding strength is sufficient. It has been proposed to test such balls by applying a flat shear tool to one side thereof. In order to avoid friction caused by the tool rubbing on the surface of the substrate, it is necessary for the tool to be just above the substrate surface.

U.S. Pat. No. 6,341,530 discloses a device for testing the force to shear a deposit of solder or gold from a substrate, for deposits having a diameter in the range 50-100 mm and being for the bonding of electrical conductors. A shear tool has a semi-cylindrical cavity, which closely approximates to the mean diameter of a range of substrates. This tool is adapted to re-shape substrates for a better fit, re-shaping occurring over 30% or less of the circumference of a deposit, and to a depth of 10% or less of the diameter of the substrate.

US 2004/0103726 discloses a tool to be installed into a test module of a bond test system to provide the capability to directly view a bond shear test. This capability enables a vision system camera coupled to magnifying optics to provide real time viewing, image capture, and vision guided automation for more effective analysis, additional analytic capability and improved ergonomics. This greatly enhances the utility of the shear test function of the bond test system.

In addition to the shear test for the bonding strength of the balls, the semiconductor devices are also required to conduct a pull test for the bonding strength of the bonding wires. However, the above-mentioned references can conduct only the shear test, not the pull test. Furthermore, the shear force is applied to the balls in the shear test, and the applied force is not stopped until the ball is removed; the pull force is applied to the boding wires in the pull test, and the applied force is not stopped until the bonding wires break off, i.e., the shear test and the pull test are destructive tests, which can not be repeated at the same condition. Therefore, it is necessary to calibrate the applied force of the test tool.

SUMMARY OF THE INVENTION

One aspect of the present invention provides an apparatus for testing the bonding strength of the electrical connection, which is equipped with rotational test head having at least two probes for conducting different bonding strength tests such as the wire-pull test and ball-shear test. Another aspect of the present invention provides a calibration device with a frictionless design for the apparatus for testing bonding strength of electrical connections.

An apparatus for testing bonding strength of electrical connection according to this aspect of the present invention comprises a platform including a two-axis drive, a device holder positioned on the two-axis drive and configured to receive an electronic device, a vertical drive positioned on the platform, a cantilever positioned on the vertical drive, and a test head connected in a rotational manner with the cantilever.

Another aspect of the present invention provides a frictionless calibration device comprising a base, two supporters positioned on the base, a shaft having two tapering ends positioned between the two supporters, and a calibration member fixed on the shaft, wherein the shaft is configured to contact the supporters in a rotational manner.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
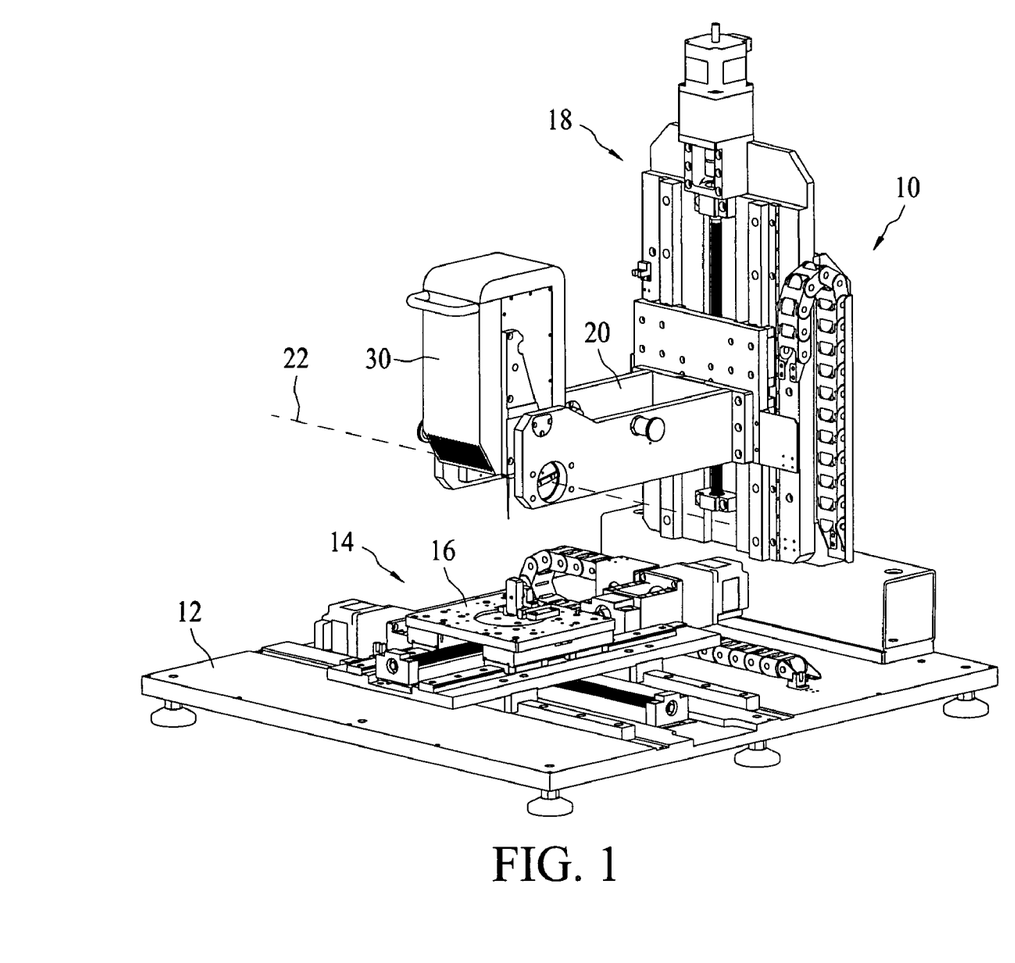
FIG. 1 and FIG. 2 illustrate an apparatus for testing bonding strength of electrical connection according to one embodiment of the present invention.
Figure 2:
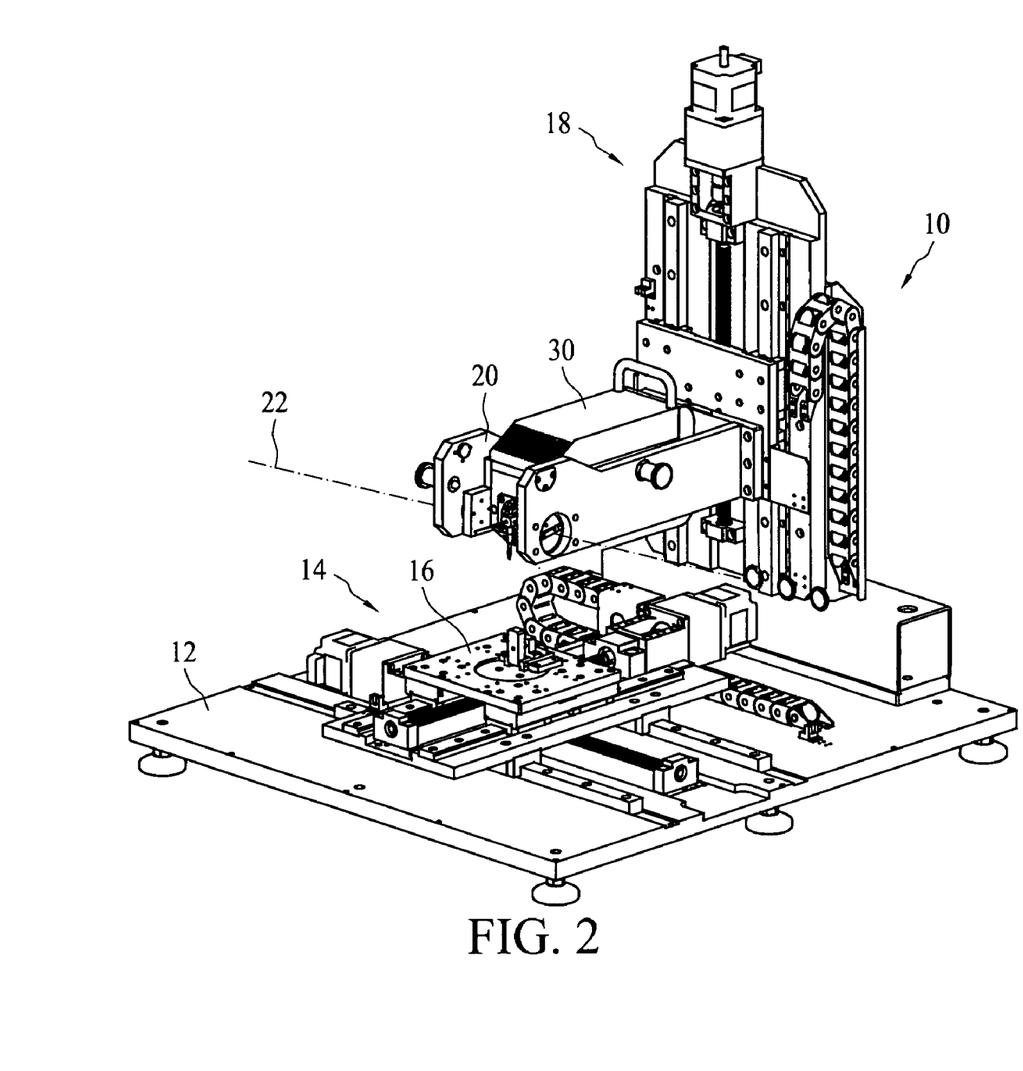

FIG. 1 and FIG. 2 illustrate an apparatus 10 for testing bonding strength of electrical connections according to one embodiment of the present invention. The apparatus 10 comprises a platform 12 including a two-axis drive 14, a device holder 16 positioned on the two-axis drive 14 and configured to receive an electronic device, a vertical drive 18 positioned on the platform 12, a cantilever 20 positioned on the vertical drive 18, and a test head 30 connected in a rotational manner with the cantilever 20. The test head 30 is configured to rotate around a shaft 22 substantially perpendicular to the cantilever 20, i.e., substantially parallel to a horizontal plane. In one embodiment of the present invention, the apparatus 10 may be incorporated with a control module such as a computer to control the movements of the two-axis drive 14 and the vertical drive 18.

Figure 3:
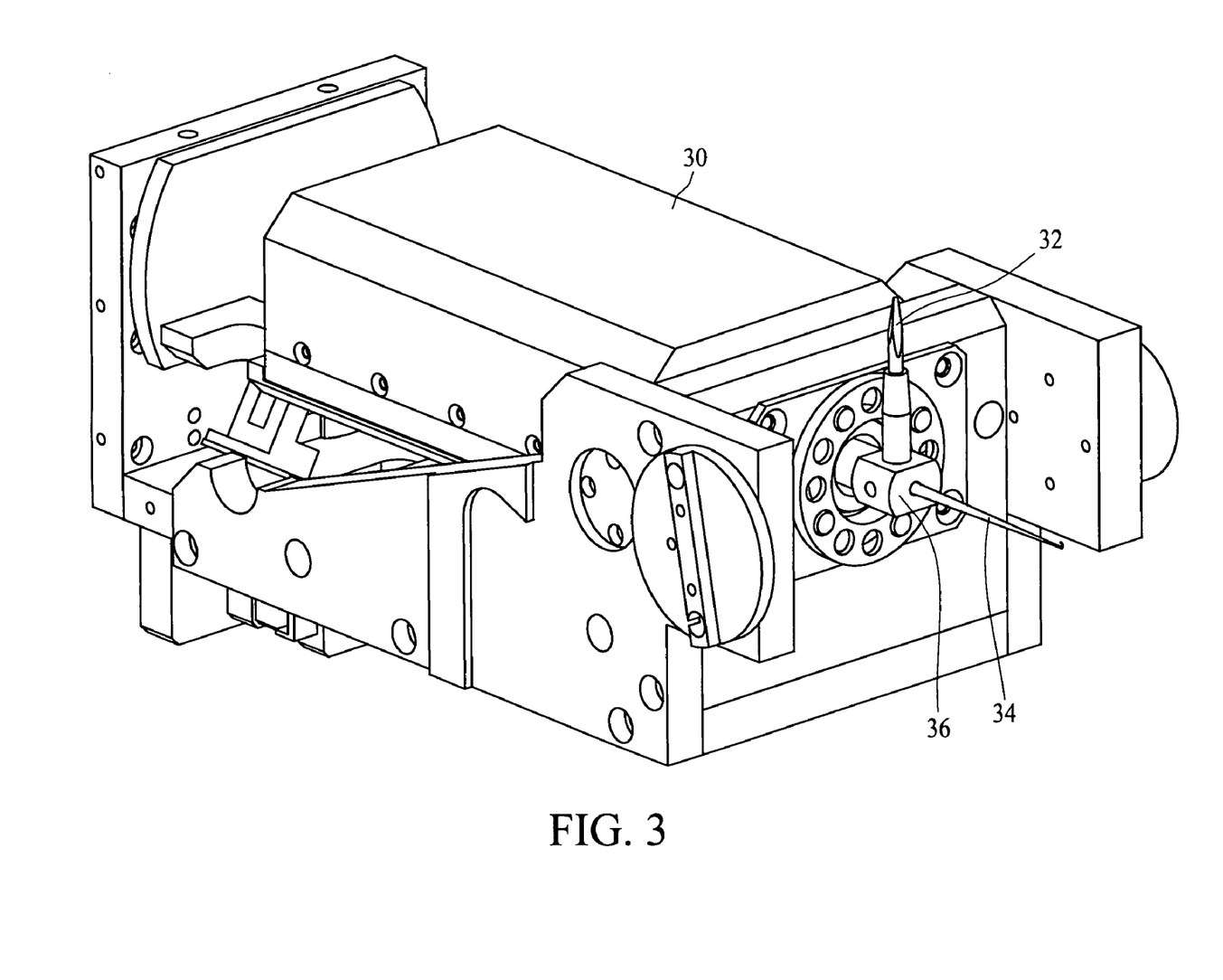
FIG. 3 and FIG. 4 illustrate a test head according to one embodiment of the present invention.
Figure 4:
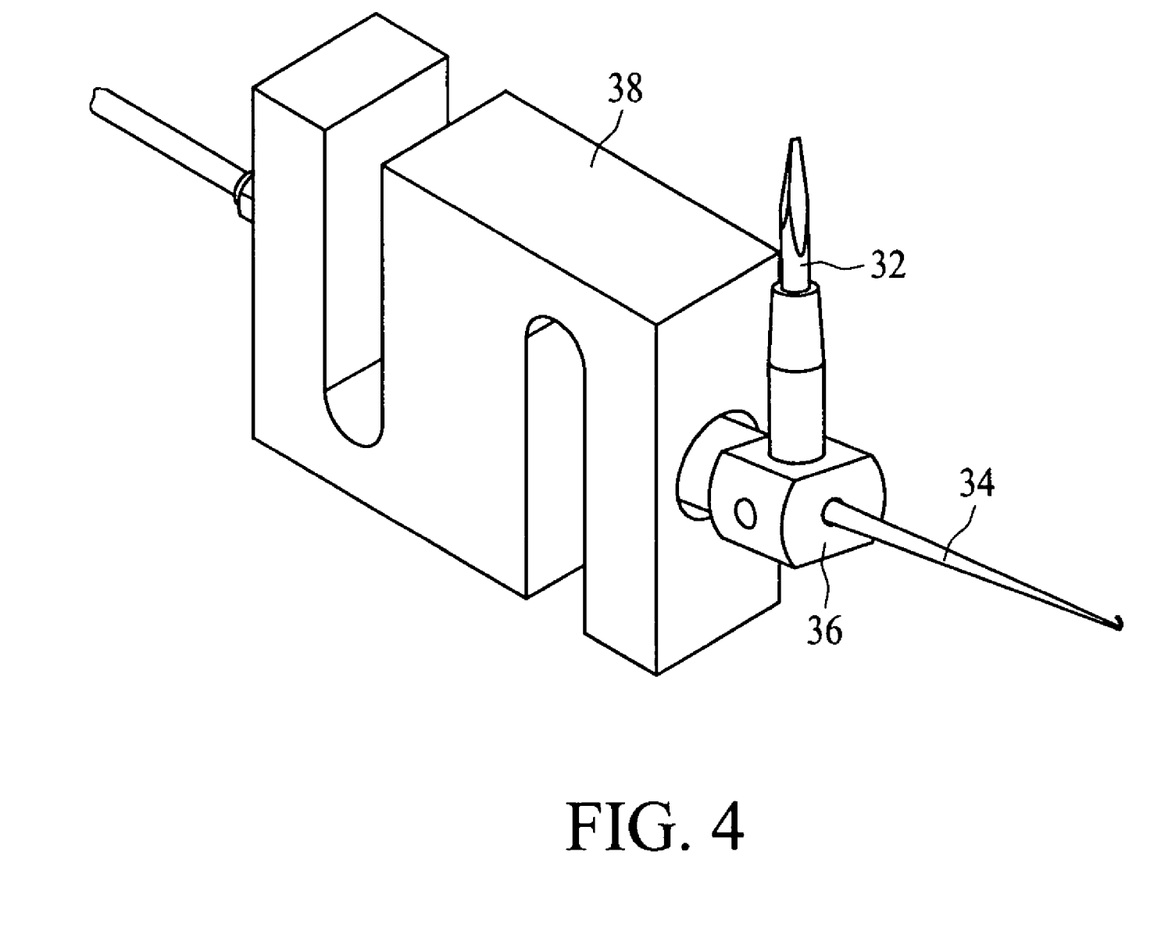

FIG. 3 and FIG. 4 illustrate the test head 30 according to one embodiment of the present invention. The test head 30 includes a first probe 32, a second probe 34 substantially perpendicular to the first probe 32, and a force sensor 38 configured to measure the force exerted on the electronic device when the test head 30 is moved. The first probe 32 and the second probe 34 are fixed on a connector 36 connected to the force sensor 38. In one embodiment of the present invention, the force sensor 38 is an S-shaped piezoelectric device.

Figure 5:
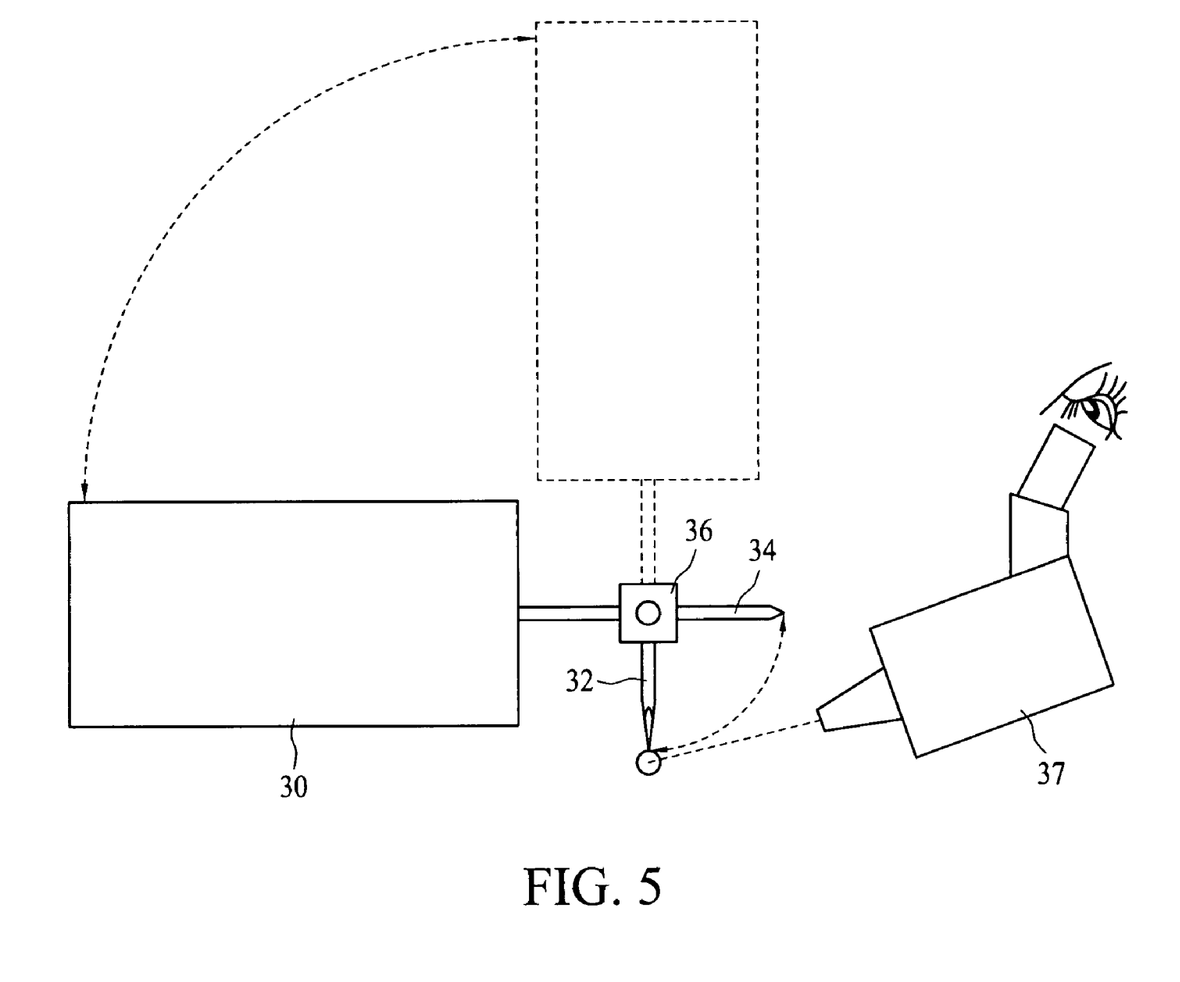
FIG. 5 illustrates the rotation operation of the test head according to one embodiment of the present invention.

FIG. 5 illustrates the rotation operation of the test head 30 according to one embodiment of the present invention. The tip position of the first probe 32 is substantially the same as that of the second probe 34 after rotating the test head 30 around the shaft 22, such that it is not necessary to calibrate the tip position after rotating the test head 30 around the shaft 22, the user can observe the tip position without adjusting the microscope 37.

Figure 6:
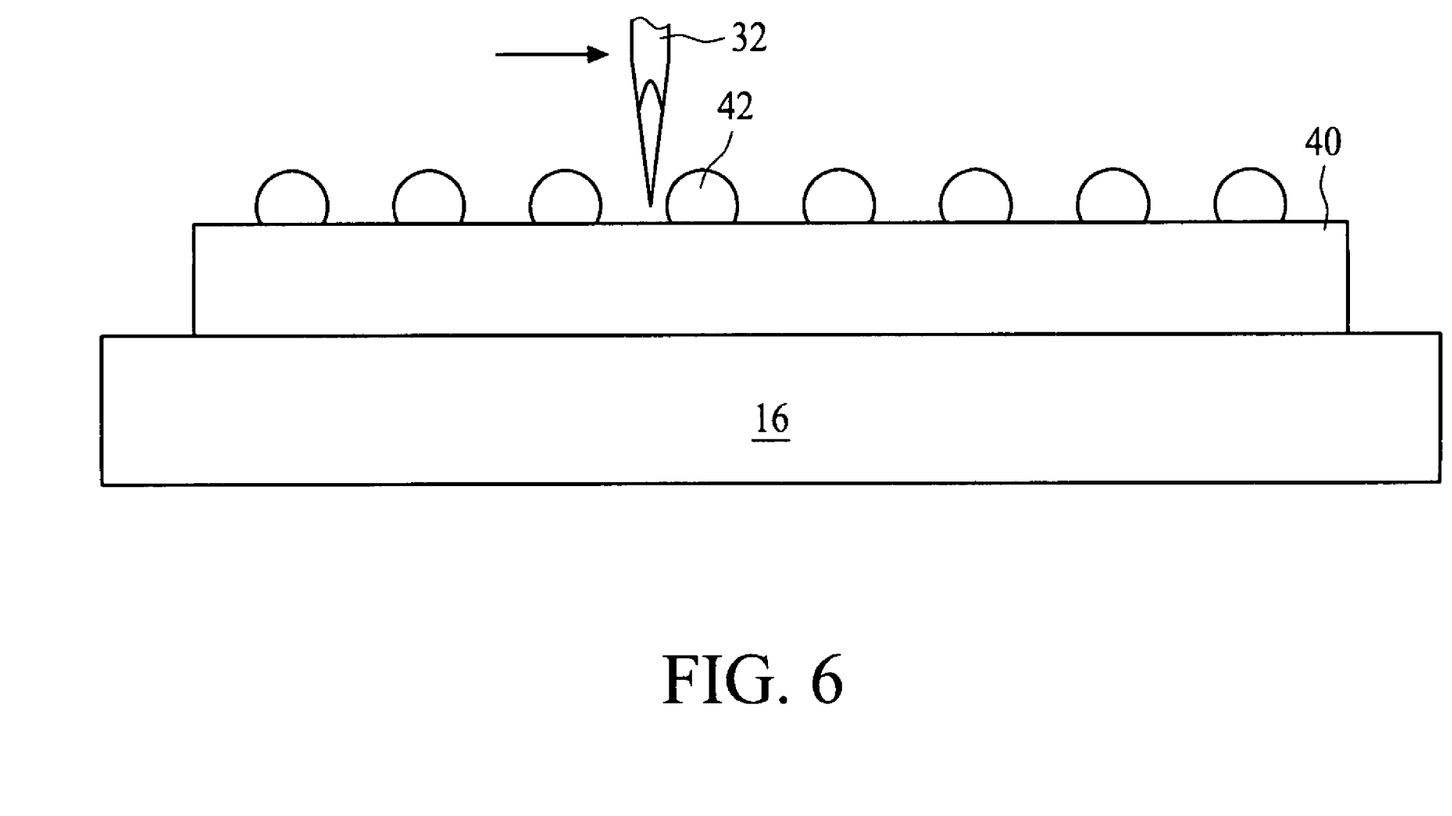
FIG. 6 illustrates the application of the apparatus to the shear testing of an electronic device according to one embodiment of the present invention.

FIG. 6 illustrates the application of the apparatus 10 to the shear testing of an electronic device 40 according to one embodiment of the present invention. The electronic device 40 includes a plurality of balls 42 such as the gold ball or solder ball, the first probe 32 is a shear probe configured to apply a shear force to the ball 42 of the electronic device 40, i.e., configured to push the ball 42 horizontally. To perform the shear test, the test head 30 is rotated around the shaft 22 such that the first probe 32 directs downward to the electronic device 40 on the device holder 16. During the shear test, the two-axis drive 14 continuously moves the device holder 16 horizontally such that the shear force applied by the shear probe 32 to the ball 42 will not stop until the ball 42 departs from the electronic device 40. The force sensor 38 will detect the applied force at the moment the ball 42 departs from the electronic device 40, and the applied force represents the bonding strength of the ball 42 to the electronic device 40.

Figure 7:
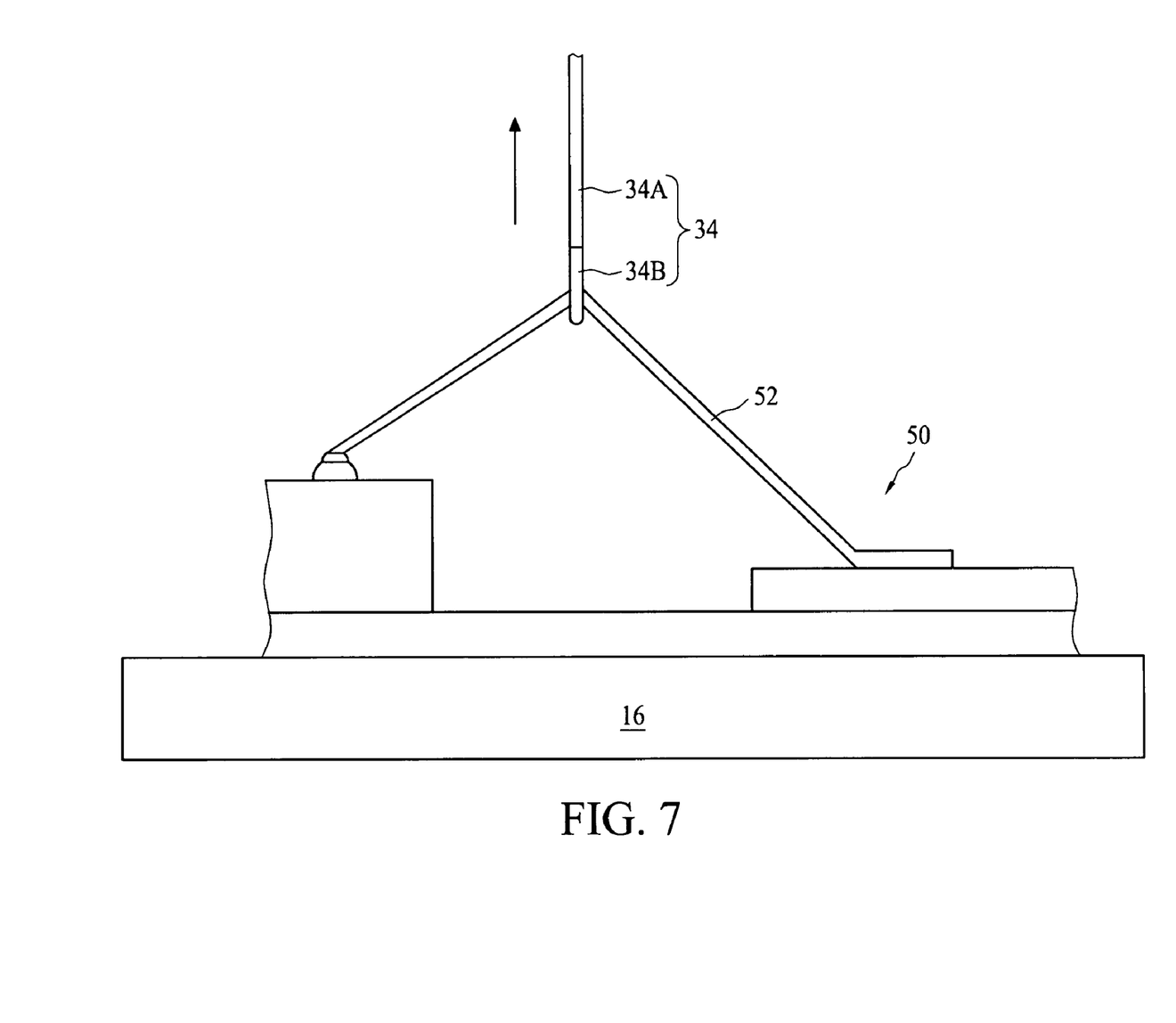
FIG. 7 illustrates the application of the apparatus to the pull testing of an electronic device according to one embodiment of the present invention.

FIG. 7 illustrates the application of the apparatus 10 to the pull testing of an electronic device 50 according to one embodiment of the present invention. The electronic device 50 includes a bonding wire 52, the second probe 34 includes a body portion 34A and a hook portion 34B configured to engage the bonding wire 52 of the electronic device 50, i.e., pull the bonding wire 52 vertically. To perform the pull test, the test head 30 is rotated around the shaft 22 such that the second probe 34 directs downward to the electronic device 50 on the device holder 16. During the pull test, the vertical drive 18 continuously moves the test head 30 vertically such that the pull force applied by the pull probe 34 to the bonding wire 52 will not stop until the bonding wire 52 breaks off. The force sensor 38 will detect the applied force at the moment the bonding wire 52 breaks off, and the applied force represents the bonding strength of the bonding wire 52 to the electronic device 50.

Figure 8:
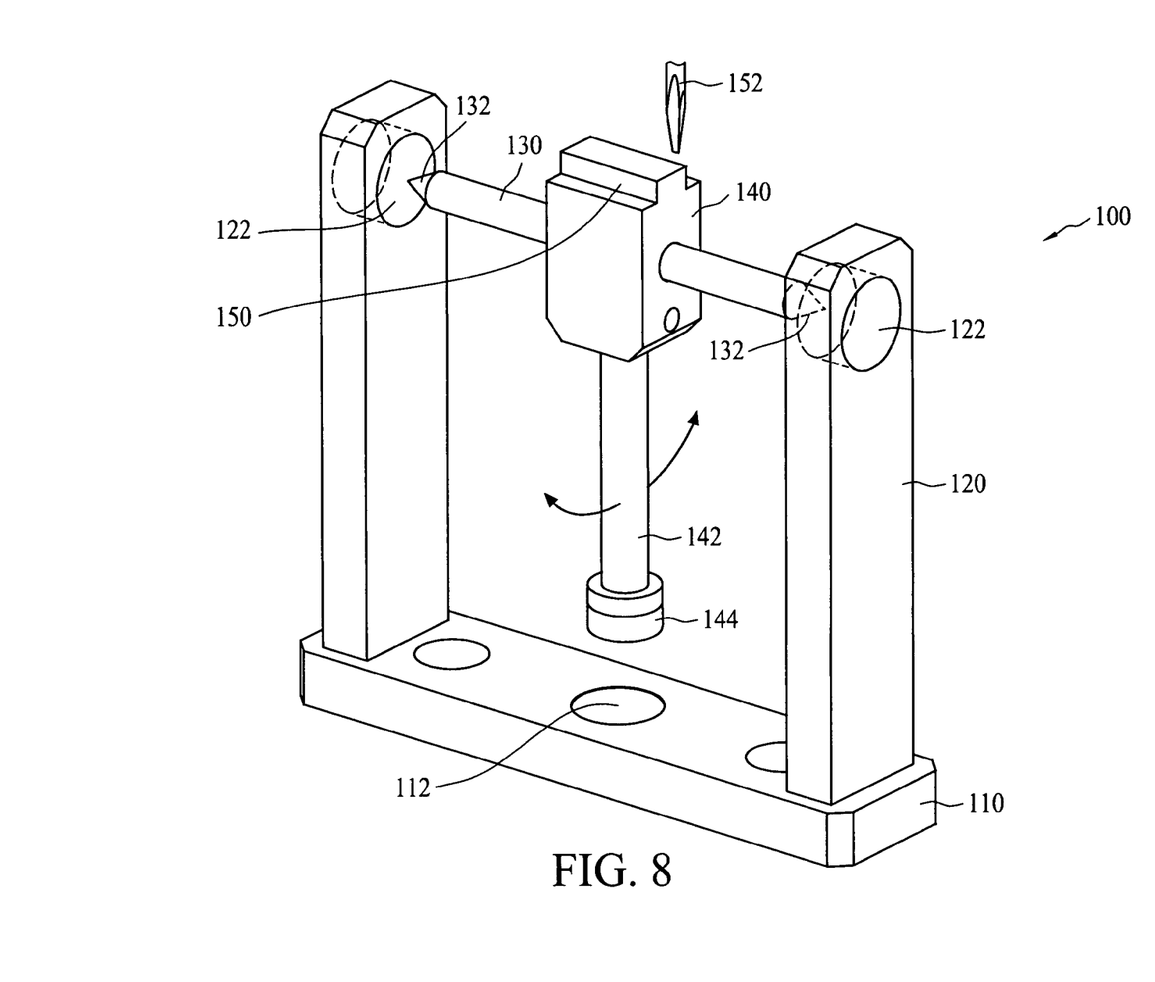
FIG. 8 illustrates a frictionless calibration device for shear force testing according to one embodiment of the present invention.

FIG. 8 illustrates a frictionless calibration device 100 for shear force testing according to one embodiment of the present invention. The frictionless calibration device 100 comprises a base 110, two supporters 120 positioned on the base 110, a shaft 130 having two tapering ends 132 positioned between the two supporters 120, and a calibration member 140 fixed on the shaft 130, wherein the shaft 130 is configured to contact the supporters 120 via the tapering ends 132 in a rotational manner. Each supporter 120 includes a magnetic device 122, and the shaft 130 is substantially perpendicular to the magnetic device 122. The shaft 130 is positioned between the supporters 120 primarily via the magnetic interaction of the magnetic device 122 on the supporters 120, and one of the tapering ends 132 of the shaft 130 may contact the magnetic device 122. In addition, the calibration member 140 includes a contact portion 150 configured to receive a probe 152 such as the shear probe 32, and the shaft 130 penetrates through the calibration member 140.

As the probe 152 moves to contact the contact portion 150 of the calibration member 140, the calibration member 140 swings, and the force sensor 38 detects the force of the probe 152 applied to the contact portion 150. The probe 152 is moved forward and backward repeatedly to contact the contact portion 150 of the calibration member 140, and the force detected by the force sensor 38 is compared to determine whether the variation of the applied force of the apparatus 10 is within a predetermined specification.

Since the shaft 130 is positioned between the supporters 120 primarily via the magnetic interaction of the magnetic device 122 on the supporters 120, the friction between the shaft 130 and the supporters 120 is reduced to a negligible degree as the shaft 130 swings during the calibration process, such that the influence of the friction is solved. In particular, in order to minimize the contact friction between the shaft 130 and the supporters 120, the two tapering ends 132 of the shaft 130 are designed to be as small as possible. In one embodiment of the present invention, the calibration member 140 includes a plummet 142 and a magnetic block 144 positioned on the plummet 142, and the base 110 includes a magnetic device 112 such as an electromagnet facing the magnetic block 144. Consequently, the swing period of the calibration member 140 can be decreased by the magnetic interaction between the magnetic device 112 and the magnetic block 144. In addition, adjusting the electrical power applied to the electromagnetic device 112 of the base 110 can adjust the magnetic force between the magnetic block 144 on the plummet 142 and the electromagnetic device 112 of the base 110 such that the swing resistance of the plummet 142 is adjustable, i.e., the calibration force of the probe 152 is adjustable.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for testing the bonding strength of electrical connections, comprising:
   a platform including a two-axis drive;
   a device holder positioned on the two-axis drive and configured to receive an electronic device;
   a vertical drive positioned on the platform;
   a cantilever positioned on the vertical drive; and
   a test head connected in a rotational manner with the cantilever;
   wherein the test head includes a force sensor;

wherein the force sensor includes a piezoelectric device; wherein the piezoelectric device is S-shaped.

2. The apparatus for testing the bonding strength of electrical connections of claim 1, wherein the force sensor configured to measure the force exerted on the electronic device when the test head is moved.

3. An apparatus for testing the bonding strength of electrical connections, comprising:
   a platform including a two-axis drive;
   a device holder positioned on the two-axis drive and configured to receive an electronic device;
   a vertical drive positioned on the platform;
   a cantilever positioned on the vertical drive; and
   a test head connected in a rotational manner with the cantilever, wherein the test head includes a first probe and a second probe substantially perpendicular to the first probe.

4. The apparatus for testing the bonding strength of electrical connections of claim 3, wherein the tip position of the first probe is substantially the same as that of the second probe after rotating the test head around the shaft.

5. The apparatus for testing the bonding strength of electrical connections of claim 3, wherein the first probe is a shear probe configured to apply a shear force to a ball of the electronic device.

6. The apparatus for testing the bonding strength of electrical connections of claim 5, wherein the shear probe is configured to push the ball horizontally.

7. The apparatus for testing the bonding strength of electrical connections of claim 3, wherein the second probe includes a hook portion configured to engage a bonding wire of the electronic device.

8. The apparatus for testing the bonding strength of electrical connections of claim 7, wherein the hook portion is configured to pull the bonding wire vertically.

9. A frictionless calibration device for shear force testing, comprising:
   a base;
   two supporters positioned on the base;
   a shaft having two tapering ends positioned between the two supporters; and
   a calibration member fixed on the shaft, wherein the shaft is configured to contact the supporters in a rotational manner.

10. The frictionless calibration device for shear force testing of claim 9, wherein the calibration member includes a plummet.

11. The frictionless calibration device for shear force testing of claim 10, further comprising a magnetic block positioned on the plummet, and the base includes magnetic device facing the magnetic end.

12. The frictionless calibration device for shear force testing of claim 9, wherein each supporter includes a magnetic device, and one of the tapering ends contacts the magnetic device.

13. The frictionless calibration device for shear force testing of claim 12, wherein the shaft is substantially perpendicular to the magnetic device.

14. The frictionless calibration device for shear force testing of claim 9, wherein the shaft penetrates through the calibration member.

15. The frictionless calibration device for shear force testing of claim 9, wherein the calibration member includes a contact portion configured to receive a probe.

* * * * *